| United States Patent [19] | [11] | Patent Number: | 4,474,824 |
|---|---|---|---|
| DeWolf, II et al. | [45] | Date of Patent: | Oct. 2, 1984 |

[54] METHODS OF PREPARING HYDROUS SILICA GELS

[75] Inventors: Robert B. DeWolf, II, Glen Burnie; Rimantas Glemza, Baltimore, both of Md.

[73] Assignee: W. R. Grace & Co., New York, N.Y.

[21] Appl. No.: 122,103

[22] Filed: Feb. 15, 1980

Related U.S. Application Data

[62] Division of Ser. No. 909,149, May 24, 1978, Pat. No. 4,303,461.

[51] Int. Cl.$^3$ .............................................. A61K 7/16
[52] U.S. Cl. ........................................ 427/2; 424/49; 252/315.6; 427/215; 423/339
[58] Field of Search ................... 252/317; 427/215, 2; 424/49; 423/335, 339

[56] References Cited

U.S. PATENT DOCUMENTS

| 1,772,055 | 8/1930 | Miller | 252/317 |
|---|---|---|---|
| 2,481,825 | 9/1949 | Connolly | 252/317 |
| 2,807,588 | 9/1957 | White | 252/317 |
| 2,856,268 | 10/1958 | Young | 252/317 |
| 3,146,076 | 8/1964 | Taluenhelmo | 34/36 |
| 3,655,580 | 4/1972 | Beau | 252/317 |
| 4,153,680 | 5/1979 | Seybert | 424/49 |
| 4,180,566 | 12/1980 | Wingall | 424/127 |

*Primary Examiner*—Sam Silverberg
*Attorney, Agent, or Firm*—Mark T. Collins

[57] ABSTRACT

Dentifrice compositions containing a hydrous silica gel having a water content of from about 20 to about 60 weight percent are disclosed. The abrasiveness of the gel is increased by contacting the gel with an alkaline medium to provide a gel pH of about 6 to about 10 and/or preparing the gel by drying and grinding a silica hydrogel that has been washed with an aqueous acidic solution having a temperature of from about 80° to about 100° F.

15 Claims, No Drawings

METHODS OF PREPARING HYDROUS SILICA GELS

This is a division of application Ser. No. 909,149, filed May 24, 1978, now U.S. Pat. No. 4,303,461.

This invention relates to dentifrice compositions containing a hydrous silica gel as a polishing and cleaning agent and to methods of preparing and treating the gel to increase its abrasiveness.

Dentifrice compositions are used with a toothbrush to remove stains, pellicle film, and food debris from the teeth. In order to accomplish this removal, dentifrice compositions generally contain a solid abrasive as a polishing and cleaning agent and a liquid phase comprising a humectant and water. The abrasive should not damage the underlying tooth material and should be compatible with the humectant and other ingredients that may be incorporated in the dentifrice composition.

Silica xerogels are used as polishing and cleaning agents in dentifrice compositions. Silica xerogels are prepared by slowly drying silica hydrogels to effect considerable shrinkage of the hydrogel structure and form a dense, rigid structure. Although silica xerogels are highly effective polishing and cleaning agents, the drying required increases the manufacturing costs and the gel structure absorbs a portion of the liquid components used in formulating the dentifrice.

In accordance with this invention, there are prepared dentifrice compositions containing from about 5 to about 50 weight percent of a hydrous silica gel having a water content of from about 20 to about 60 weight percent, and an average particle size of from about 1 to about 40 microns. In order to increase their abrasiveness, the gels may have a pH of from about 6 to about 10 provided by contacting the gels with an alkaline medium. Increased abrasiveness is also provided by preparing the gels by washing a silica hydrogel with an aqueous acidic solution having a temperature of from 80° to about 100° F. for a period of time sufficient to reduce the total salts content of the gel to less than about 5 weight percent and drying and grinding the hydrogel to a desired water content and particle size.

The gels may be rapidly dried to reduce manufacturing costs and reduce the amount of humectant required to form a given volume of dentifrice because of the lower absorption into the water-containing pores. The dentifrice compositions of this invention provide effective cleaning and polishing as measured by the radioactive dentin abrasion values (RDA) determined in accordance with the procedure of the American Dental Association described in Hefferren, *J. Dent. Res.*, pp. 563–513 (July-August 1976) with the following exceptions. The RDA values are determined using a slurry containing 6.25 grams of the hydrous silica gel instead of the 10.0 grams of the abrasive powder used in the American Dental Association procedure. Also, the RDA values throughout this specification are based on a RDA value of 500 for the calcium pyrophosphate reference standard instead of the value of 100 assigned to this reference standard in the American Dental Association procedure. The hydrous silica gels of this invention preferably have an RDA value of at least about 400. The hydrous silica gels prepared from hydrogels washed at about 80° to about 100° F. and contacted with an alkaline medium in accordance with this invention have an RDA value of at least about 600.

The hydrous silica gels that are used as the polishing and cleaning agents in the dentifrice compositions of this invention may be prepared from acid-set silica hydrogels. Silica hydrogel may be produced by reacting an alkali metal silicate and a mineral acid in an aqueous medium to form a silica hydrosol and allowing the hydrosol to set to a hydrogel. When the quantity of acid reacted with the silicate is such that the final pH of the reaction mixture is acidic, the resulting product is considered an acid-set hydrogel. Sulfuric acid is the most commonly used acid, although other mineral acids such as hydrochloric acid, nitric acid, or phosphoric acid may be used. Sodium or potassium silicate may be used, for example, as the alkali metal silicate. Sodium silicate is preferred because it is the least expensive and most readily available. The concentration of the aqueous acidic solution is generally from about 5 to about 70 percent by weight and the aqueous silicate solution commonly has an $SiO_2$ content of about 6 to about 25 weight percent and a weight ratio of $SiO_2$ to $Na_2O$ of from about 1:1 to about 3.4:1.

The mineral acid solution and the alkali metal silicate solution are mixed to form a silica hydrosol. The relative proportions and concentrations of the reactants are controlled so that the hydrosol contains about 6 to about 20 weight percent $SiO_2$ and has a pH of less than about 5 and commonly between about 1 to about 3. Generally, continuous processing is employed and both reactants are metered separately into a high speed mixer. The reaction may be carried out at any convenient temperature, for example, from about 15 to about 80° C. and is generally carried out at ambient temperatures.

The silica hydrosol will set to a hydrogel in generally about 5 to about 90 minutes and is then washed with an aqueous acidic solution to remove residual alkali metal salts which are formed in the reaction. For example, when sulfuric acid and sodium silicate are used as the reactants, sodium sulfate is entrapped in the hydrogel. Prior to washing, the gel is normally cut or broken into pieces in a particle size range of from about ½ to about 3 inches. The gel may be washed with an aqueous solution of mineral acid such as sulfuric acid, hydrochloric acid, nitric acid, or phosphoric acid or a medium strength acid such as formic acid, acetic acid, or propionic acid.

The wash solution contains an amount of the acid sufficient to provide a pH of from about 2.0 to about 5.0, preferably from about 2.5 to about 4.5. The temperature of the wash solution affects the properties of the hydrous silica gel product. Generally, the temperature of the solution is from about 80° to about 200° F. Preferably, the solution is at a temperature of from about 80° to about 100° F. in order to enhance further the abrasiveness of the hydrous silica gel product. It is believed that lower wash temperatures reduce bonding between micelles and facilitate shrinkage on subsequent drying.

The gel is washed for a period sufficient to reduce the total salts content to less than about 5 weight percent. The gel may have, for example, a $Na_2O$ content of from about 0.5 to about 3 weight percent and a $SO_4$ content of from about 0.05 to about 3 weight percent, based on the dry weight of the gel. The period of time necessary to achieve this salt removal varies with the flow rate of the wash medium and the configuration of the washing apparatus. Generally, the period of time necessary to achieve the desired salt removal is from about 6 to about 30 hours. Although the effect is not as great as that of decreased wash temperatures, shorter washing periods increase the abrasiveness of the hydrous silica gel products because bonding between micelles is further reduced and thus shrinkage on subsequent drying is enhanced. Thus, it is preferred that the hydrogel be washed with the aqueous acidic solution at a temperature of from about 80° to about 100° F. for about 6 to about 15 hours, especially for about 6 to about 12 hours.

The gel pH increases as the salts are removed by the acid wash. In order to prepare hydrous silica gels suitable for use in the dentifrice compositions of this invention, the final gel pH upon completion of washing as measured in a 5 weight percent aqueous slurry of the gel, may range from about 2.5 to about 5.

The washed silica hydrogel generally has a water content, as measured by loss on ignition at 1750° F., of from 60 to about 75 weight percent and a particle size ranging from about 1 micron to about 50 millimeters. The hydrogel is then dried to the desired water content of from about 20 to about 60 weight percent, preferably from about 35 to about 60 weight percent. Oven drying, rotary drying, cascade drying or some other known drying method may be employed. For example, the washed hydrogel may be dried in a rotary or cascade dryer at an inlet air temperature of from about 590° to about 610° F. and an outlet air temperature of about 120° to about 125° F. for a residence time of about 4 hours to produce a product containing 44 weight percent water. The gel is ground to an average particle size of from about 1 to about 40 microns, preferably of from about 5 to about 20 microns, for use in dentifrice compositions. The average particle size referred to throughout this specification is determined in a Microtrak particle size analyzer. An average particle size with no more than about 1 weight percent larger than 50 microns is preferred for use in dentifrice compositions. The hydrogels may be ground by a variety of methods under a variety of conditions to provide the suitable average particle size. Since water is usually removed during grinding, the hydrogel may be dried to within about 10 weight percent or higher of the desired final water content and the remaining water removed during grinding. When the water content of the hydrogel is greater than about 70 weight percent, the hydrogel may be pre-dried in any suitable dryer at a temperature and for a time sufficient to reduce the water content of the hydrogel to below about 70 weight percent to remove surface moisture and facilitate feeding of the hydrogel into the heated mill.

In a preferred embodiment, the silica hydrogel is simultaneously dried and ground in a mill in the presence of heated air in order to provide the desired water content and average particle size suitable for use in dentifrice compositions. For example, the hydrogels may be concurrently ground and dried in a mechanical grinding device, such as an impact mill, for example, a rotary hammer mill, in which a moving stream of heated air is introduced. In this concurrent operation, the mill may be operated using air at essentially atmospheric pressure with inlet temperatures of from about 200° to about 500° F. and outlet air temperatures of from about 80° to about 150° F. An especially suitable mill is an air-classifying hammer mill, such as the MikroPul ACM-10 mill, in which the inlet air stream is heated.

The hydrous silica gel product after drying and grinding may be contacted with an alkaline medium to increase its abrasiveness. The alkaline medium may be, for example, ammonia, an organic amine, an alkali metal hydroxide, or an alkali metal carbonate. Preferably, the hydrous silica gel is contacted with an ammoniacal medium. The ammoniacal medium may be gaseous ammonia, aqueous ammonia, or other aqueous ammoniacal mediums containing, for example, aliphatic amines and particularly alkyl amines and alkylene diamines, such as ethyl amine, ethylene diamine, propyl amine, propylene diamine, diethylene diamine, and the like. Ammonia is strongly adsorbed by the gel so that ammonia-containing solutions of widely varying concentrations and prepared from a wide variety of ammonia-containing compounds may be used.

The hydrous silica gel is contacted with the alkaline medium in an amount sufficient to provide a gel having a pH of from about 6 to about 10 and preferably from about 8 to about 9.5. The pH is measured in a 5 weight percent aqueous slurry of the gel. The use of a gaseous alkaline medium is preferred because of the greater uniformity and speed of adsorption. The gel may be contacted with the alkaline medium by circulating the gas or spraying the solution over the gel until the gel has adsorbed the required amount of base and achieved the desired pH.

In a preferred embodiment of this invention, the gel is contacted with gaseous anhydrous ammonia upon exit from the mill. Preferably, the gel is contacted with the ammonia not more than about 1 minute after milling. The air stream containing the gel has a temperature of from about 80° to about 150° F. so that contact with the ammonia provides rapid absorption into the gel particles.

The hydrous silica gels are employed in the dentifrice compositions of this invention in a polishing and cleaning effective amount. Generally, the gel comprises about 5 to about 50 percent, preferably about 5 to about 20 percent, by weight of the dentifrice composition.

The dentifrice of the invention can also further contain as optional ingredients a soap or synthetic detergent as a surface tension depressant; flavoring materials; buffers; sweeteners such as saccharin; humectants; preservatives; and harmless coloring materials, in proportions to give any desired effect. A fluoride such as stannous fluoride, zirconium fluoride, or sodium fluosilicate can be included. Each of these fluorine compounds contains available fluorine which can be taken up by the enamel of the teeth. These are conventional components of dentifrices, and materials suitable for this purpose need not be enumerated for they are well known to those skilled in the dentifrice art.

In a preferred embodiment, the dentifrice is in the form of a paste, and in this event it will comprise the hydrous silica gel and a humectant and a binder in amounts to give the dentifrice a smooth texture and good flowability. Glycerin and sorbitol are preferred humectants, but ethyl alcohol, mineral oil, corn syrup, glucose and invert sugars, glycols and honey can also be employed. As binders, there can be used gum tragacanth, sodium carboxymethylcellulose, hydroxyethylcellulose, Indian gum, Irish moss or carragheen and its derivatives, starch, acacia gums, locust bean gum, pectin and petrolatum. Those skilled in the dentifrice art know other humectants and binders. It is preferred to incorporate in the dentifrice composition a silica aerogel having an average particle size of below about four microns, for example, from about one to about three microns. The aerogel helps to body the toothpaste but has minimal abrasiveness. Generally, the dentifrice composition may contain from about 0.5 to about 20 weight percent of the silica aerogel. A pyrogenic silica may also be used as a thixotropic agent.

The degree of translucency of the product can be increased or decreased by varying the amount and composition of the humectant materials. For example, certain flavoring materials could be more soluble in one humectant system than in another. Obviously, insoluble flavoring materials will decrease translucency, and appropriate changes in the humectant system to enhance solubility would simultaneously enhance translucency. Additionally, it has been found that greater translucency is obtained when the refractive index of the humectant system is adjusted appropriately. Thus, a system containing appropriate amounts of glycerin, sorbitol and/or water can give a transparent product. The effect can be attributed to a closer matching of the refractive indices of the solid and liquid portions of the dentifrice.

The use of the hydrous silica polishing and cleansing ingredient in the dentifrice compositions of the invention permits the incorporation therein of oral health agents such as germicides, antibiotics and astringents. Typical examples thereof include tyrothrycin, chlorophyllins, hexachlorophene, the sarcosides and astringent salts.

Such oral health agents are employed in a beneficial amount normally ranging from about 0.01 percent to about 2 percent by weight of paste dentifrice. The humectants are generally employed in an amount from about 5 percent to about 75 percent by weight of the dentifrice, the binders in an amount from about 0.5 percent to about 30 percent by weight of the dentifrice, flavoring agents in an amount from about 0.1 percent to about 5 percent by weight of the dentifrice, water in an amount from about 4 percent to about 60 percent by weight of the dentifrice, surface tension depressants in an amount from about 0.01 percent to about 6 percent by weight of the dentifrice, and preservatives in an amount from about 0.01 percent to about 2 percent of the dentifrice.

The dentifrices are prepared by blending the components together, with deaeration being necessary for the translucent and transparent toothpastes.

The compositions and methods of this invention are illustrated by the following examples. All parts and percentages in the examples are by weight unless otherwise noted.

EXAMPLE 1

A 36° Baume aqueous sulfuric acid solution and a 36.5° Baume aqueous sodium silicate solution were pumped into a high speed mixer at flow rates of 18 gallons per minute and 53 gallons per minute respectively. An excess of sulfuric acid was maintained to the extent of 0.6N. The resulting silica hydrosol had an $SiO_2$ content of 18 percent and a pH of about 1.5. The silica hydrosol was deposited onto a moving belt and set to a hydrogel in 15 minutes. 1,000 pounds of the hydrogel were dropped into a wash basket and washed with an aqueous solution of sulfuric acid having a pH of 4 and a temperature of 88° to 90° F. at a rate of 4 gallons per minute for 12 hours.

After washing, the washed products of four repeat runs were cascade dried and blended. The blend had a total volatiles content of 64 percent and $Na_2O$ and $SO_4$ contents of 0.15 and 0.28 percent respectively. An aqueous slurry containing 5 percent of the hydrogel had a pH of 4.1.

A series of samples of the blended material were then fed to a MikroPul ACM-10 mill into which was introduced a heated air stream at a rate of about 700 actual cubic feet per minute. The feed rates and air inlet temperatures were varied to provide the desired degree of drying. As determined in a Microtrak particle size analyzer, the average particle size of the product ranged from about 12 to about 15 microns. In half of the runs, anhydrous gaseous ammonia was injected into the outlet conduit of the mill and contacted with the gel to provide the desired pH increase. The properties of the various hydrous silica gel products are shown in Table I. % TV is the total volatiles lost on ignition at 1750° F.

TABLE 1

| | | | Wt. % Dry Basis | | | Wt. % on wet screen | |
|---|---|---|---|---|---|---|---|
| % TV | pH (5% slurry) | RDA | $Na_2O$ | $SO_4$ | $NH_3$ | 325 mesh | 100 mesh |
| | | $NH_3$ TREATED | | | | | |
| 53.7 | 8.6 | 760 | .14 | .11 | .43 | 1.63 | 0 |
| 44.6 | 8.4 | 860 | .11 | .19 | .35 | 1.12 | 10 ppm |
| 39.0 | 8.4 | 930 | .13 | .29 | .34 | 1.45 | 10 ppm |
| | | UNTREATED | | | | | |
| 58.5 | 4.7 | 160 | .36 | .69 | | 1.91 | 10 ppm |
| 42.4 | 4.2 | 360 | .24 | .41 | | 1.09 | 10 ppm |
| 37.0 | 4.1 | 440 | .15 | .31 | | 1.49 | 50 ppm |

EXAMPLE 2

A series of silica hydrogels were prepared in accordance with the procedure of Example 1. All the gels were washed with an aqueous solution of sulfuric acid having a pH of 4.0 at a rate of 4 gallons per minute. Type A gels were washed with the solution at 90° F. for 8.5 hours to a gel pH of 3.2. Type C gels were washed with the solution at 180° F. for 7.5 hours to a gel pH of 4.0. All the gels were ground and dried in the MikroPul ACM-10 and contacted with ammonia in accordance with the procedure of Example 1. The properties of the hydrous silica gel products are shown in Table 2.

TABLE 2

| | % TV | pH (5% slurry) | Wt. % Dry Basis | | | Wt. % on Wet Screen | | Microtrak APS (microns) | RDA |
|---|---|---|---|---|---|---|---|---|---|
| | | | $Na_2O$ | $SO_4$ | $NH_3$ | 325 mesh | 100 mesh | | |
| A | 55.0 | 8.3 | .29 | .37 | .37 | 1.88 | 0 | 14.8 | 675 |
| A | 47.1 | 7.5 | .61 | 1.26 | .24 | 1.69 | 0 | 14.9 | 815 |
| A | 38.3 | 7.5 | .71 | 1.25 | .23 | .32 | 0 | 14.3 | 970 |
| C | 58.8 | 8.5 | .04 | .07 | — | .07 | 0 | 12.3 | 260 |

TABLE 2-continued

|   | % TV | pH (5% slurry) | Wt. % Dry Basis Na$_2$O | SO$_4$ | NH$_3$ | Wt. % on Wet Screen 325 mesh | 100 mesh | Microtrak APS (microns) | RDA |
|---|------|----------------|-------------------------|--------|--------|------------------------------|----------|-------------------------|-----|
| C | 46.5 | 8.8 | .04 | .03 | — | .19 | 0 | — | 540 |
| C | 37.6 | 8.7 | .05 | .01 | — | .06 | 0 | 12.5 | 865 |

EXAMPLE 3

Silica hydrogels were prepared in accordance with the procedure of Example 1, washed by the Type A procedure of Example 2 to a total Na$_2$O and SO$_4$ content of about 2.0 percent, and ground and dried in the MikroPul ACM-10 to Microtrak average particle sizes ranging from 9.0 to 12 microns. The ground and dried gels were treated with varying amounts of ammonia to vary the gel pH and untreated control samples were prepared. The properties of the gels are shown in Table 3.

TABLE 3

| Sample No. | % TV | pH | RDA |
|------------|------|-----|-----|
| 1 | 24 | 7.5 | 990 |
| CONTROL | 31 | 3.2 | 580 |
| 2 | 31.5 | 6.1 | 780 |
| 3 | 31 | 6.9 | 930 |
| 4 | 28 | 7.7 | 1070 |
| 5 | 35 | 7.0 | 790 |
| 6 | 34.5 | 7.5 | 860 |
| 7 | 33 | 8.2 | 950 |
| CONTROL | 39 | 3.2 | 325 |

EXAMPLE 4

In accordance with the procedure of Example 2, a series of Type A and C gels were prepared without ammonia treatment. The properties of the gel products are shown in Table 4.

TABLE 4

|   | % TV | Wt. % Dry Basis Na$_2$O | SO$_4$ | Wt. % on Wet Screen 325 mesh | 100 mesh | Microtrak APS (microns) | RDA |
|---|------|-------------------------|--------|------------------------------|----------|-------------------------|-----|
| A | 56.9 | .99 | 1.82 | 1.70 | 10 ppm | 16.1 | 190 |
| A | 45.8 | .39 | .82 | .13 | 0 | 13.1 | 270 |
| A | 38.8 | .42 | .70 | .33 | 10 ppm | 13.5 | 430 |
| C | 55.9 | .04 | .09 | .11 | 0 | 13.8 | 80 |
| C | 46.4 | .04 | .03 | .14 | 0 | 13.2 | 265 |
| C | 39.4 | .04 | .10 | .25 | .02 | 12.1 | 485 |

EXAMPLE 5

In accordance with the procedure of Example 2, a series of Type A gels were prepared without ammonia treatment to illustrate the relationship between approximate total volatiles and RDA as shown in Table 5.

TABLE 5

| Approximate % TV | RDA |
|------------------|-----|
| 56 | 190 |
| 49 | 170 |
| 45 | 270 |
| 38 | 395* |
| 28 | 610 |
| 21 | 640 |

*average of two values

A dentifrice composition of this invention may be prepared by combining the following components in the following proportions.

| Component | Parts by Weight |
|-----------|-----------------|
| NH$_3$ Treated Hydrous Silica Gel of Example 1 at 39.0 TV % | 20.00 |
| Sodium Carboxymethylcellulose | 0.30 |
| Saccharin | 0.20 |
| 70% Sorbitol - 30% Water Mixture | 70.04 |
| Sodium Benzoate | 0.08 |
| Colorant (about 1% solution) | 0.53 |
| Flavor and Chloroform | 1.85 |
| 21% Sodium Lauryl Sulfate - 79% Glycerine Mixture | 7.00 |

What is claimed is:

1. A method of preparing a hydrous silica gel which comprises setting a silica hydrosol having a pH of less than about 5 to an acid-set silica hydrogel, washing the acid-set silica hydrogel with an aqueous acidic solution to provide a silica hydrogel having a pH of from about 2.5 to about 5, drying the washed hydrogel to a water content of from about 20 to about 60 weight percent, grinding the washed hydrogel to an average particle size of from about 1 to about 40 microns, and contacting the dried gel with an alkaline medium in an amount sufficient to provide a gel having a pH of from about 6 to about 10.

2. The method of claim 1 in which the hydrogel is dried to a water content of from about 35 to about 60 weight percent.

3. The method of claim 1 in which the gel is contacted with an alkaline medium in an amount sufficient to provide a gel having a pH of from about 8 to about 9.5.

4. The method of claim 1 in which the gel is contacted with an ammoniacal medium.

5. The method of claim 1 in which the gel is contacted with gaseous ammonia.

6. The method of claim 1 in which the gel is contacted with an alkaline medium comprising an alkali metal hydroxide.

7. The method of claim 1 in which the hydrogel is washed with an aqueous acidic solution having a temperature of from about 80° to about 200° F.

8. The method of claim 7 in which the hydrogel is washed with an aqueous acidic solution having a temperature of from about 80° to about 100° F.

9. The method of claim 7 in which the aqueous acidic solution has a pH of from about 2.0 to about 5.0.

10. The method of claim 7 in which the aqueous acidic solution has a pH of from about 2.5 to about 4.5.

11. The method of claim 7 which the hydrogel is washed for a period of time sufficient to reduce the total salts content of the hydrogel to less than about 5 weight percent.

12. The method of claim 7 in which the hydrogel is washed for about 6 to about 15 hours.

13. The method of claim 7 in which the hydrogel is washed for about 6 to about 12 hours.

14. The method of claim 1 in which the hydrogel is simultaneously dried and ground in an impact mill into which a moving stream of heated air is introduced.

15. The method of claim 14 in which the mill is an air classifying hammer mill and the heated air has an inlet temperature of from about 200° to about 500° F. and an outlet temperature of from about 80° to about 150° F.

* * * * *